(12) United States Patent
Matthews et al.

(10) Patent No.: US 8,518,306 B2
(45) Date of Patent: Aug. 27, 2013

(54) METHOD FOR MAKING SELF-ASSEMBLING, COLLAGEN-BASED MATERIAL FOR CORNEAL REPLACEMENT

(75) Inventors: W. Garrett Matthews, Temple Terrace, FL (US); August Heim, Tampa, FL (US); Thomas J. Koob, Tampa, FL (US)

(73) Assignees: University of South Florida, Tampa, FL (US); Shriners Hospitals for Children, Tampa, FL (US)

( * ) Notice: Subject to any disclaimer, the term of this patent is extended or adjusted under 35 U.S.C. 154(b) by 0 days.

(21) Appl. No.: 13/107,299

(22) Filed: May 13, 2011
(Under 37 CFR 1.47)

(65) Prior Publication Data

US 2011/0217460 A1   Sep. 8, 2011

Related U.S. Application Data

(62) Division of application No. 11/685,528, filed on Mar. 13, 2007, now abandoned.

(60) Provisional application No. 60/767,234, filed on Mar. 13, 2006.

(51) Int. Cl.
*B29D 11/00* (2006.01)
*B29C 41/08* (2006.01)

(52) U.S. Cl.
USPC .............................. 264/1.1; 264/309; 427/162

(58) Field of Classification Search
USPC ..................... 264/1.1, 1.7, 2.7, 309; 427/2.1, 427/2.24, 162
See application file for complete search history.

(56) References Cited

U.S. PATENT DOCUMENTS

| | | |
|---|---|---|
| 4,693,715 A | 9/1987 | Abel, Jr. |
| 5,108,428 A | 4/1992 | Capecchi et al. |
| 5,420,248 A | 5/1995 | Devictor et al. |
| 5,836,313 A | 11/1998 | Perez et al. |
| 6,106,552 A | 8/2000 | Lacombe et al. |
| 6,277,397 B1 | 8/2001 | Shimizu |
| 6,335,007 B1 | 1/2002 | Shimizu et al. |
| 6,974,679 B2 | 12/2005 | Andre et al. |
| 6,976,997 B2 | 12/2005 | Noolandi et al. |
| 7,084,082 B1 | 8/2006 | Shimizu |
| 2002/0037940 A1 * | 3/2002 | Koob et al. ...................... 521/55 |
| 2005/0019488 A1 | 1/2005 | Braithwaite et al. |
| 2005/0067287 A1 * | 3/2005 | Fuerst et al. ...................... 205/79 |

OTHER PUBLICATIONS

Trotter et al., Cell and Tissue Research, Mar. 1994, Springer-Verlag, Mar. 1994; 275 (3):451-8.
Trotter, J.A. et al. "Growth of Sea Cucumber Collagen Fibrils Occurs at the Tips and Centers in a Coordinated Manner" *Journal of Molecular Biology*, Dec. 18, 1998, 284(5):1417-1424.
Trotter, J.A. et al. "Echinoderm Collagen Fibrils Grow by Surface-Nucleation-and-Propagation from Both Centers and Ends" *Journal of Molecular Biology*, Jul. 14, 2000, 300(3):531-540.
Supplementary European Search Report dated Jul. 26, 2012 in European Application No. 20070758434.0, filed Mar. 13, 2007.

* cited by examiner

*Primary Examiner* — Mathieu D. Vargot
(74) *Attorney, Agent, or Firm* — Saliwanchik, Lloyd & Eisenschenk

(57) ABSTRACT

A material derived from sea cucumber collagen fibrils is suitable for use in corneal replacements or as an implantable contact lens. To produce material, the collagen fibrils are centrifuged into orthogonal stacks of lamellae comprised of aligned fibrils. The resulting structure is a transparent film of arbitrary thickness very similar in structure to mammalian corneal tissue.

9 Claims, No Drawings

METHOD FOR MAKING SELF-ASSEMBLING, COLLAGEN-BASED MATERIAL FOR CORNEAL REPLACEMENT

CROSS-REFERENCE TO RELATED APPLICATION

This application is a divisional of U.S. application Ser. No. 11/685,528, filed Mar. 13, 2007, now abandoned, which claims the benefit under 35 U.S.C. §119 of U.S. Provisional Patent Application Ser. No. 60/767,234, filed Mar. 13, 2006, which is incorporated herein by reference in its entirety.

FIELD OF THE INVENTION

The present invention relates to the field of corneal replacements. This new material is useful for developing biologically derived artificial corneas for implantation or as coatings for contact lenses.

BACKGROUND OF THE INVENTION

The cornea provides protection for the intraocular contents of the eye and refracts and focuses light onto the retina. Many diseases and conditions can lead to opacity of the cornea, resulting in blindness. These include trauma, infections, inflammation, previous ocular surgery, and genetic conditions.

Keratoplasty, or corneal transplantation, is a surgical procedure where a damaged or diseased cornea is replaced. The replacement material is typically donated corneal tissue from a recently deceased individual, but there is a shortage in the donor tissue available. The replacement corneal tissue has to be obtained from a deceased donor and preserved until the time of transplantation. The tissue has to be harvested within 12 hours of death, and used within approximately seven days. The success rate also depends on the existing underlying condition of the eye.

Up to 10 million people worldwide suffer from blindness or other disorders resulting from corneal dysfunctions. However, only approximately 100,000 conical transplants are performed annually. The disparity in these numbers results directly from a lack of appropriate donor tissue.

Although an artificial cornea would solve the problem of corneal tissue availability and other problems, previous attempts at artificial corneas have had various deficiencies. One challenge of developing an artificial cornea is to design and manufacture a structure that is optically clear centrally and biocompatible peripherally that would allow for cellular integration. This has proven difficult in practice. Artificial corneas that have been implanted in patients have had severe complications, such as endophthalmitis (intraocular infections), extrusion, glaucoma (uncontrolled elevated intraocular pressure), epithelial downgrowth, uveitis (intraocular inflammation) and tissue necrosis. These complications may be partly due to poor tissue adhesion between the keratoprothesis, and the recipient tissue, resulting in severe irreversible loss of vision.

Many synthetic corneas have been used. Synthetic corneas and their production and use are described in, for example, U.S. Pat. No. 6,976,997 to Noolandi et al., U.S. Pat. No. 6,106,552 to Lacombe et al., U.S. Pat. No. 5,108,428 to Capecchi et al., and U.S. Pat. No. 4,693,715 to Abel, Jr., all of which are hereby incorporated by reference.

These replacement corneas suffer from the problems of being expensive or incompatible with many patients. Thus, there still exists a need in the art of corneal replacements for a material that can be made inexpensively and biologically compatible.

BRIEF SUMMARY OF THE INVENTION

The present invention provides a material for corneal replacements that is inexpensive and biologically compatible. It has the optical and biological properties of the tissue being replaced, and it has the ability to be generated inexpensively and in large quantities. Thus, it will help alleviate the lack of suitable corneal replacements. It may also have the additional benefit of reducing the life-long dependency of implant patients on immunosuppressant medications. The disclosed material is produced from collagen, the same molecular substance from which native cornea is derived, and has optical and mechanical properties similar to that of the cornea. The process is rapid, robust, and relatively simple; thus, it can be easily scaled up for mass production.

In addition, the material of the present invention is potentially suitable for use as onlays for implantable contact lenses.

DETAILED DISCLOSURE OF THE INVENTION

The present invention is a material suitable for corneal transplants having similar optical and biological properties as compared to the tissue being replaced. The disclosed material is produced from collagen, the same molecular substance from which native cornea is derived, and has optical and mechanical properties similar to that of the cornea The present invention is a simple and efficient method to self-assemble collagen fibrils, exemplified herein by collagen fibrils isolated from sea cucumber, into orthogonal stacks of lamellae comprising aligned fibrils. The resulting structure is a transparent film of arbitrary thickness very similar in structure to mammalian corneal tissue. This new material is useful for developing biologically derived artificial corneas for implantation or as coatings for contact lenses.

An aqueous emulsion of extracted collagen fibrils, for example, from the *Cucumaria frondosa*, class Holothurioidea, phylum Echinodermata, is centrifuged at high speed, and the resulting pellet is lyophilized onto a template. The template is a surface possessing the desired geometry and may be made of a polymeric or plastic material, among others. A film of compacted layers of aligned fibrils is formed. The film retains the shape of the underlying template surface onto which it was molded. Judicious choice of the shape of this template surface results in films of defined geometries, as will be readily appreciated by one of ordinary skill in the art. Once the desired geometry is known based on the intended recipient's vision, the template surface can be selected appropriately to provide a corneal replacement suitable for that specific recipient. Additionally, multiple deposition processes may be performed to increase the thickness of the film as desired.

The self-assembled planar alignment of the banded fibrils within lamellae and the orthogonal relative orientation of these lamellar structures are presumed to be caused by the spatial restrictions and local registration of glycosaminoglycan chains located circumferentially along the fibril surface. The orthogonal sheets form a necessary crystal structure during the sheering processes created by centrifugation and lyophilization, creating optical transparency comparable or superior to modern synthetic cornea materials used in keratoplasties.

The present invention uses native, intact collagen fibrils. By using fibrils in which the proteoglycan components are entirely present, structures that mimic native cornea form by means that appear to be inherent in the system. By using a material that is biologically derived, and one which may easily be rendered biocompatible, the subject invention is a product that is significantly improved relative either to materials derived from donors or from abiotic sources.

In addition, the present invention may be used as onlays for implantable contact lenses. The same process is used as with the corneal replacement. As may be desired, a different geometry or thickness may be used.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method for producing a material suitable for ophthalmic purposes, comprising:
    obtaining collagen fibrils isolated from an organism of the phylum Echinodermata; and
    forming the collagen fibrils into a transparent film, wherein forming the collagen fibrils into a transparent film comprises:
        centrifuging an aqueous preparation of the collagen fibrils to obtain a pellet of the collagen fibrils; and
        lyophilizing the pellet on a template, thereby forming the transparent film on the template.

2. The method according to claim 1, further comprising producing a desired geometry for the transparent film.

3. The method according to claim 2, wherein producing a desired geometry for the transparent film comprises selecting a shape for the template.

4. The method according to claim 2, wherein the desired geometry for the transparent film comprises a geometry suitable for corneal replacement.

5. The method according to claim 2, wherein the desired geometry for the transparent film comprises a geometry suitable for use in conjunction with or as part of a contact lens.

6. The method according to claim 1, further comprising repeatedly depositing collagen fibrils onto the template to achieve a desired thickness of the transparent film.

7. The method according to claim 1, wherein the template comprises a polymeric or plastic material.

8. The method according to claim 1, wherein the organism is *Cucumaria frondosa*.

9. The method according to claim 1, wherein the transparent film comprises the collagen fibrils aligned in a lamellar structure of orthogonal stacks.

* * * * *